United States Patent [19]

Guembel et al.

[11] Patent Number: 5,177,222

[45] Date of Patent: Jan. 5, 1993

[54] 1,1-DIALKOXY-2-OXO-6-ARYL-3,5-ALKADIENES

[75] Inventors: Helmut Guembel, Ludwigshafen; Joachim Paust, Neuhofen; Karin Sperling-Vietmeier, Neustadt; Rainer Becker, Bad Duerkheim, all of Fed. Rep. of Germany

[73] Assignee: BASF Aktiengesellschaft, Ludwigshafen, Fed. Rep. of Germany

[21] Appl. No.: 608,844

[22] Filed: Nov. 5, 1990

[30] Foreign Application Priority Data

Nov. 18, 1989 [DE] Fed. Rep. of Germany ....... 3938468

[51] Int. Cl.⁵ .................... C07C 69/76; C07C 211/00; C07D 319/06
[52] U.S. Cl. .................................. 549/372; 549/450; 560/45; 560/53; 564/305; 568/308; 568/313; 568/328
[58] Field of Search ............. 568/308, 313, 328; 549/372, 450, 313; 560/53, 45; 564/305

[56] References Cited

U.S. PATENT DOCUMENTS 4,515,774 5/1985 Conner et al.

FOREIGN PATENT DOCUMENTS 0418655 3/1981 European Pat. Off. ............ 549/313
2728242 1/1979 Fed. Rep. of Germany
3206586 4/1983 Fed. Rep. of Germany

OTHER PUBLICATIONS

Tsuge et al. "Synthesis and Acid-Catalyzed Ring Opening of Ketons", *Bull. of The Chemical Society of Japan*, vol. 61, pp. 2897–2908 (1988).

Konrad et al. "New Substance for the UV Range", *Parfum. Kosmet* 64(6) pp. 317–318, and 320–322 (1983).
Chemical Abstracts, Band 109, No. 19, Nov. 7, 1988, Columbus, Ohio, USA Terumo Corp "5-Phenyl-2,4-pentadien-1-one derivatives and their use as platelet aggregation inhibitors and lipoxygenase inhibitors" Seite 680, Spalte 2, Zusammenfassung-Nr. 170 035b & Jpn. Kokai Tokkyo Koho JP 62,281,839 (87 281 839).

*Primary Examiner*—José G. Dees
*Assistant Examiner*—Keith MacMillan
*Attorney, Agent, or Firm*—Oblon, Spivak, McClelland, Maier & Neustadt

[57] ABSTRACT

1,1-Dialkoxy-2-oxo-6-aryl-3,5-alkadienes of the general formula I

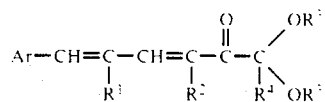

where
Ar is a phenyl, biphenyl or naphthyl radical which may be substituted by one, two or three $C_1$-$C_4$-alkyl groups, $C_1$-$C_4$-alkoxy groups, hydroxyl groups, phenoxy groups, amino groups which may be mono- or di-$C_1$-$C_4$-alkyl-substituted, halogen atoms or a methylenedioxy group, the substituents being identical or different,
$R^1$ is hydrogen or $C_1$-$C_8$-alkyl,
$R^2$ is hydrogen, $C_1$-$C_4$-alkyl, $C_1$-$C_{10}$-alkoxycarbonyl or $C_1$-$C_{10}$-acyl,
the radicals $R^3$ are $C_1$-$C_8$-alkyl groups which may be bonded to one another with formation of a five-membered or six-membered ring and
$R^4$ is hydrogen or $C_1$-$C_4$-alkyl, are used as sunscreen agents in cosmetic preparations.

5 Claims, No Drawings

1,1-DIALKOXY-2-OXO-6-ARYL-3,5-ALKADIENES

The present invention relates to 1,1-dialkoxy-2-oxo-6-aryl-3,5-alkadienes of the general formula I

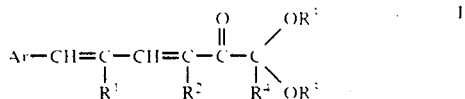

where

Ar is a phenyl, biphenyl or naphthyl radical which may be substituted by one, two or three $C_1$-$C_4$-alkyl groups, $C_1$-$C_4$-alkoxy groups, hydroxyl groups, phenoxy groups, amino groups which may be mono- or di-$C_1$-$C_4$-alkyl-substituted, halogen atoms or a methylenedioxy group, the substituents being identical or different, $R^1$ is hydrogen or $C_1$-$C_8$-alkyl, $R^2$ is hydrogen, $C_1$-$C_4$-alkyl, $C_1$-$C_{10}$-alkoxycarbonyl or $C_1$-$C_{10}$-acyl, the radicals $R^3$ are $C_1$-$C_8$-alkyl groups which may be bonded to one another with formation of a five-membered or six-membered ring and $R^4$ is hydrogen or $C_1$$C_4$-alkyl.

The present invention furthermore relates to a process for the preparation of the compounds I and their use as sunscreen agents in cosmetic preparations.

DE-A 27 28 242 discloses pyruvic acid and levulinic acid condensates of the general formula IV

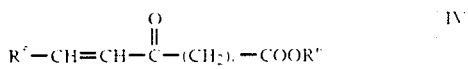

where $R^5$ is aryl or 2-arylvinyl, $R^6$ is hydrogen, $C_1$-$C_4$-alkyl or a salt-forming cation and n is 0 or 2. The compounds IV are used as cosmetic sunscreen agents for the UV-A range.

DE-C 32 06 586 describes 2-acyl-5-phenyl-2,4-pentadienoic esters of the general formula V

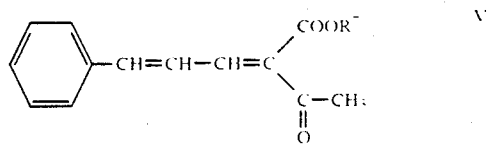

where $R^7$ is $C_1$-$C_8$-alkyl or alkoxyalkyl having a total of 4 carbon atoms. The esters V are recommended as sunscreen agents for cosmetic and industrial applications.

U.S. Pat. No. 4,515,774 relates to dialkyl cinnamylidenemalonates of the general formula VI

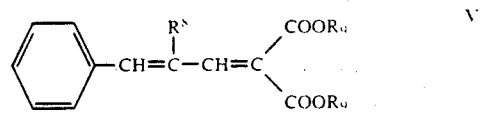

where $R^8$ is hydrogen or $C_1$-$C_8$-alkyl and $R^9$ is methyl or ethyl. The compounds VI are used as sunscreen agents for human skin.

There is an increasing need for sunscreen agents for cosmetic preparations, which can be used as UV-A filters and whose absorption maxima should therefore be in the range from about 330 to 380 nm, as is the case for the compounds IV to VI. To achieve the desired effect using a very small amount, such sunscreen agents should additionally have a high specific absorbance. Furthermore, sunscreen agents for cosmetic preparations must meet many other requirements, for example good solubility in cosmetic oils, high stability of the emulsions prepared with them and little intrinsic odor or color. However, the compounds IV to VI meet these requirements for UV-A filter substances for cosmetic applications only to a limited extent.

It is an object of the present invention to provide sunscreen agents for cosmetic preparations for the protection of human skin from light, which stabilizers meet all the stated requirements to a greater extent than the known agents of this type.

We have found that this object is achieved by the 1,1-dialkoxy-2-oxo-6-aryl-3,5-alkadienes I.

Other suitable aryl radicals Ar are, in particular, phenyl which may be substituted by one, two or three $C_1$-$C_4$-alkyl groups or by one or two $C_1$-$C_4$-alkoxy groups, hydroxyl groups or di-($C_1$-$C_4$-alkyl)-amino groups, or an unsubstituted biphenyl or naphthyl radical.

Examples of Ar are:

phenyl, o-, m- or p-tolyl, o-, m- or p-ethylphenyl, m- or p-cumyl, m- or p-tert-butylphenyl, 2,3-, 2,4-, 2,5-, 2,6-, 3,4 TM or 3,5-dimethylphenyl, mesityl, o-, m- or p-methoxyphenyl, o-, m- or p-ethoxyphenyl, m- or p-tert-butoxyphenyl, 2,3-, 2,4-, 2,5-, 2,6-, 3,4- or 3,5-dimethoxyphenyl, o-, m- or p-hydroxyphenyl, 2,3-, 2,4-, 2,5-, 2,6-, 3,4- or 3,5-dihydroxyphenyl, 3-hydroxy-4-methoxyphenyl, m- or p-phenoxyphenyl, o-, m- or p-aminophenyl, o-, m- or p-(N-methylamino)-phenyl, o-, m- or p-(N,N-dimethylamino)-phenyl, o-, m- or p-chlorophenyl, 2,4-dichlorophenyl, o-, m- or p-bromophenyl, 2,3- or 3,4-methylenedioxyphenyl, 2-, 3- or 4-biphenyl and α- or β-naphthyl.

$R^1$ is preferably hydrogen or $C_1$-$C_5$-alkyl, for example methyl, ethyl, n-propyl, n-butyl or n-pentyl. Hydrogen is particularly preferred.

$R^2$ is preferably hydrogen, $C_1$-$C_4$-alkyl, such as methyl, ethyl, n-propyl or n-butyl, $C_1$-$C_4$-alkoxycarbonyl, e.g. methoxycarbonyl or ethoxycarbonyl, or $C_1$-$C_4$-acyl, such as acetyl, propionyl or butyryl. Hydrogen or $C_1$-$C_4$-alkyl is particularly preferred.

The alkyl radicals $R^3$ may be different or preferably identical and are each $C_1$-$C_8$-alkyl, preferably $C_1$-$C_4$-alkyl, such as methyl, ethyl, n-propyl, n-butyl or 2-ethylhexyl; the two radicals $R^3$ may be bonded to one another with formation of a five-membered or six-membered ring, for example a 1,3-dioxolan, 1,3-dioxane, 5,5-dimethyl-1,3-dioxane or 5-n-butyl-5-ethyl-1,3-dioxane ring.

$R^4$ is preferably hydrogen or methyl but may also be a $C_2$-$C_4$-alkyl, e.g. ethyl, n-propyl or n-butyl.

The novel compounds I can occur as cis/transisomer mixtures with respect to the two olefinic double bonds or as pure isomers. The cis/trans-isomerism of the compounds I has no effect on their possible cosmetic use.

The novel compounds I can advantageously be prepared by aldole condensation of an aldehyde of the general formula II

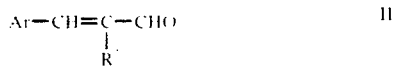

$$Ar-CH=C-CHO \quad \text{II}$$
$$\quad\quad | $$
$$\quad\quad R$$

with a methylglyoxal monoacetal derivative of the general formula III

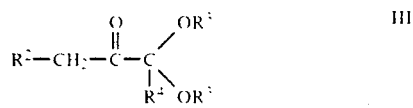

in a conventional manner under basic reaction conditions.

The reaction is usually carried out in an organic solvent, for example in an alcohol, such as methanol, ethanol, isopropanol or n-butanol, an ether, such as diethyl ether, methyl tert-butyl ether, diisopropyl ether, tetrahydrofuran or dioxane, or in a hydrocarbon, such as toluene or xylene. Examples of suitable bases are sodium hydroxide, potassium hydroxide, sodium methylate, sodium ethylate, sodium tert-butylate, potassium tert-butylate, sodium amide, sodium dimethylamide, sodium diisopropylamide, lithium diisopropylamide or sodium hydride. As a rule, the reaction is carried out at atmospheric pressure and at from 0° to 150° C., in particular from 0° to 80° C.

The novel compounds I are used as sunscreen agents in cosmetic formulations for protection from the sun. Such sunscreen preparations may be in liquid, pasty or solid form, for example as water-in-oil creams, oil-in-water creams and lotions, aerosol foam creams, gels, oils, grease pens, powders, sprays or alcoholic aqueous lotions.

The present invention furthermore relates to cosmetic preparations which contain from 0.1 to 10, preferably from 1 to 7, % by weight, based on the total cosmetic preparation, of one or more of the novel compounds I as sunscreen agents, the compounds I being used in conventional carriers or diluents, for example as a solution in an oil.

Conventional oil components in the cosmetics industry are, for example, liquid paraffin, glyceryl stearate, isopropyl myristate, diisopropyl adipate, cetylstearyl 2-ethylhexanoate, hydrogenated polyisobutene, vaseline, caprylic acid/capric acid triglycerides, microcrystalline wax, lanolin and stearic acid.

Together with the compounds I, it is possible concomitantly to use further conventional sunscreen agents, such as
2-hydroxy-4-methoxybenzophenone,
2-hydroxy-4-methoxybenzophenone-5-sulfonic acid,
ethyl p-aminobenzoate reacted with 25 moles of ethylene oxide,
2-ethylhexyl p-methoxycinnamate,
2-ethylhexyl p-(N,N-dimethylamino)-benzoate,
2-phenylbenzimidazole-5-sulfonic acid,
3-(4-methylbenzylidene)-camphor or
2,4,6-trianilino-p-(carbo-2'-ethylhex-1'-yloxy)-1,3,5-triazine.

in the conventional amounts, and it is even possible for the sunscreen action to be reinforced by a synergistic effect.

Conventional cosmetic assistants which are suitable additives are, for example, emulsifiers, such as fatty alcohol ethoxylates, sorbitan fatty acid esters or lanolin derivatives, thickeners, such as carboxymethylcellulose or crosslinked polyacrylic acid, preservatives and perfumes.

The novel 1,1-dialkyl-2-oxo-6-aryl-3,5-alkadienes I have a particularly high absorption power in the range of UV-A radiation. They can also advantageously be used in combination with UV-B filter substances. Furthermore, they are readily soluble in cosmetic oils and can easily be incorporated into cosmetic formulations. The emulsions prepared using the novel compounds have, in particular, high stability and a pleasant feel on the skin.

The compounds I are virtually colorless and odorless. Commercial UV-A filter substances currently available are yellow and also tend to stain articles of clothing. This can be avoided by using the novel compounds.

Preparation Examples

EXAMPLE 1

5,5-Dimethyl-2-(2-methyl-5-phenyl-2,4-pentadienoyl)-1,3-dioxane 7.2 g of a 30% strength by weight solution of sodium methylate in methanol were added dropwise to a solution of 52.9 g of cinnamaldehyde and 68.9 g of 5,5-dimethyl-2-propionyl-1,3-dioxane in 200 ml of methanol in the course of 15 minutes at 0–5° C., and the mixture was stirred for a further 2 hours at 0–5° C. Thereafter, the reaction solution was seeded with a few crystals of the product and stirred overnight at room temperature. After the precipitate had been filtered off under suction and washed with cold methanol, 29.8 g of the product were obtained in the form of colorless crystals of melting point 122–125° C.

Spectroscopic data: IRυ(C=O)=1,661 cm$^{-1}$
UV $\lambda_{max}$=332 nm, $E^{1\%}_{1\,cm}$=1.380

EXAMPLE 2

2-Methyl-2-(5-phenyl-2,4-pentadienoyl)-1,3-dioxolan 4.0 g of a 15% strength by weight potassium hydroxide solution were added dropwise to a solution of 26.4 g of cinnamaldehyde and 26.0 g of 2-acetyl-2-methyl-1,3-dioxolan in 100 ml of methanol in the course of 10 minutes at from 20° to 25° C., and the mixture was stirred for a further 4 hours at from 20° to 25° C. Thereafter, the solvent was distilled off, the residue was taken up in 200 ml of tert-butyl methyl ether and the solution was washed with water and dried over sodium sulfate After the solvent had been distilled off, the crude product was distilled at from 150° to 155° C. and at 0.04 mbar.

12.0 g of the product were obtained in the form of a pale yellow oil.

Spectroscopic data: IRυ(C=O)=1,691 cm$^{-1}$
UV $\lambda_{max}$=331 nm, $E^{1\%}_{1\,cm}$=1.290

Examples of Use

EXAMPLE 3

Water-in-Oil Cream

A water-in-oil (w/o) sunscreen cream has the following composition:
12.0 g of diisopropyl adipate 10.0 g of isopropyl myristate
8.0 g of unsaturated glycerol sorbitan fatty acid ester
5.0 g of vaseline
2.0 g of the compound from Example 1
2.0 g of hydrogenated castor oil reacted with 7 moles of ethylene oxide
2.0 g of dodecanol reacted with 45 moles of ethylene oxide
2.0 g of microcrystalline wax
0.7 g of magnesium sulfate heptahydrate
0.5 g of magnesium stearate
0.5 g of aluminum stearate
0.3 g of a preservative
50.0 g of water

EXAMPLE 4

Oil-in-Water Cream

An oil-in-water (o/w) sunscreen cream has the following composition:

12.0 g of glyceryl stearate
10.0 g of caprylic acid/capric acid triglyceride
10.0 g of diisopropyl adipate
3.0 g of glycerol
2.0 g of the compound from Example 1
1.0 g of a mixture of a higher saturated fatty alcohol, reacted with 6 moles of ethylene oxide, and stearyl alcohol
1.0 g of a higher saturated fatty alcohol, reacted with 25 moles of ethylene oxide
0.5 g of a preservative
60.5 g of water

We claim:

1. A 1,1-dialkoxy-2-oxo-6-aryl-3,5-alkadiene of the formula I

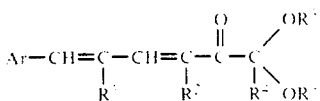

where
Ar is a phenyl, biphenyl or naphthyl radical which may be substituted by one, two or three $C_1$-$C_4$-alkyl groups, $C_1$-$C_4$-alkoxy groups, hydroxyl groups, phenoxy groups, amino groups which may be mono- or di-$C_1$-$C_4$-alkyl-substituted, halogen atoms or a methylenedioxy group, the substituents being identical or different, $R^1$ is hydrogen or $C_1$-$C_5$-alkyl, $R^2$ is hydrogen, $C_1$-$C_4$-alkyl, $C_1$-$C_{10}$-alkoxycarbonyl or $C_1$-$C_{10}$-acyl, the radicals $R^3$ are $C_1$-$C_5$-alkyl groups which may be bonded to one another with formation of a five-membered or six-membered ring and $R^4$ is hydrogen or $C_1$-$C_4$-alkyl.

2. A compound I as claimed in claim 1, in which Ar is phenyl which may be substituted by one, two or three $C_1$-$C_4$-alkyl groups or by one or two $C_1$-$C_4$-alkoxy groups, hydroxyl groups or di-($C_1$-$C_4$-alkyl)-amino groups, or is an unsubstituted biphenyl or naphthyl radical, $R^1$ is hydrogen or $C_1$-$C_5$-alkyl, $R^2$ is hydrogen, $C_1$-$C_4$-alkyl, $C_1$-$C_4$-alkoxycarbonyl or $C_1$-$C_4$-acyl, the radicals $R^3$ are $C_1$-$C_4$-alkyl groups which may be bonded to one another with formation of a five-membered or six-membered ring and $R^4$ is hydrogen or $C_1$-$C_4$-alkyl.

3. A process for the preparation of a compound I as claimed in claim 1, wherein an aldehyde of the formula II

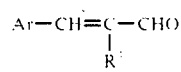

is reacted with a methylglyoxal monoacetal derivative of the formula III

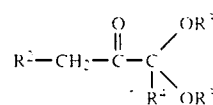

in a conventional manner under basic reaction conditions.

4. 5,5-Dimethyl-2-(2-methyl-5-phenyl-2,4-pentadienoyl)-1,3-dioxane.

5. 2-Methyl-2-(5-phenyl-2,4-pentadienoyl)-1,3-dioxolan.

* * * * *